(12) United States Patent
Teicher et al.

(10) Patent No.: US 8,469,901 B2
(45) Date of Patent: Jun. 25, 2013

(54) METHOD FOR DIAGNOSING ADHD AND RELATED BEHAVIORAL DISORDERS

(75) Inventors: Martin H. Teicher, Rye, NH (US); Kyoko Ohashi, Arlington, MA (US)

(73) Assignee: The McLean Hospital Corporation, Belmont, MA (US)

( * ) Notice: Subject to any disclaimer, the term of this patent is extended or adjusted under 35 U.S.C. 154(b) by 1132 days.

(21) Appl. No.: 11/732,526

(22) Filed: Apr. 4, 2007

(65) Prior Publication Data

US 2008/0021351 A1 Jan. 24, 2008

Related U.S. Application Data

(60) Provisional application No. 60/788,946, filed on Apr. 4, 2006.

(51) Int. Cl.
*A61B 5/103* (2006.01)
*A61B 5/117* (2006.01)

(52) U.S. Cl.
USPC .......................................................... 600/595

(58) Field of Classification Search
USPC .......................................................... 600/595
See application file for complete search history.

(56) References Cited

U.S. PATENT DOCUMENTS

| | | | |
|---|---|---|---|
| 6,475,161 B2 | 11/2002 | Teicher et al. |
| 6,554,439 B1 | 4/2003 | Teicher et al. |
| 6,579,234 B2 | 6/2003 | Lowen et al. |
| 6,685,652 B1 | 2/2004 | Teicher et al. |
| 6,994,670 B2 | 2/2006 | Teicher et al. |
| 2003/0233032 A1 | 12/2003 | Teicher et al. |
| 2004/0220493 A1 | 11/2004 | Teicher et al. |
| 2004/0243328 A1 | 12/2004 | Rapp et al. |
| 2009/0005648 A1 | 1/2009 | Teicher et al. |

FOREIGN PATENT DOCUMENTS

| | | |
|---|---|---|
| WO | WO 01/87142 | 11/2001 |
| WO | WO 2005/074801 | 8/2005 |
| WO | WO 2006/023964 | 3/2006 |
| WO | WO 2006/029021 | 3/2006 |

OTHER PUBLICATIONS

Anderson et al., "Effects of Methylphenidate on Functional Magnetic Resonance Relaxometry of the Cerebellar Vermis in Boys with ADHD," *Am. J. Psychiatry.* 159: 1322-1328, 2002.

Anderson et al., "Sex Differences in Dopamine Receptors and Their Relevance to ADHD," *Neuroscience and Biobehavioral Reviews.* 24: 137-141, 2000.

Castellanos et al., "Varieties of Attention-Deficit/Hyperactivity Disorder-Related Intra-Individual Variability," *Biol. Psychiatry.* 57: 1416-1423, 2005.

Glod et al., "Relationship Between Early Abuse, Posttraumatic Stress Disorder, and Activity Levels in Prepubertal Children," *J. Am. Acad. Child Adolescent Psychiatry.* 34: 1384-1393, 1996.

Heiser et al., "Objective Measurement of Hyperactivity, Impulsivity, and Inattention in Children with Hyperkinetic Disorders Before and After Treatment with Methylphenidate," *European Child & Adolescent Psychiatry.* 13: 100-104, 2004.

(Continued)

*Primary Examiner* — Brian Szmal
*Assistant Examiner* — H. Q. Nguyen
(74) *Attorney, Agent, or Firm* — Clark & Elbing LLP

(57) ABSTRACT

The invention features methods and systems for the diagnosis of ADHD and related disorders. The methods and systems of the invention can also be used to ascertain how much benefit an individual would derive from a particular therapy.

21 Claims, 3 Drawing Sheets

OTHER PUBLICATIONS

Ohashi et al., "Children with ADHD Have Multi-Second Spike-Wave Bursts of Movement During a Vigilance Task That Are Suppressed by Methylphenidate," *NCDEU 46th Annual Meeting: Large Clinical Trials and Evidence-Based Practice,* Session II-7 (2006).

Teicher, "Actigraphy and Motion Analysis: New Tools for Psychiatry," *Harvard Rev. Psychiatry.* 3: 18-35, 1995.

Teicher et al., "Functional Deficits in Basal Ganglia of Children With Attention-Deficit/Hyperactivity Disorder Shown With Functional Magnetic Resonance Imaging Relaxometry," *Nature Medicine.* 6: 470-473, 2000.

Teicher et al., "Novel Strategy for the Analysis of CPT Data Provides New Insight into the Effects of Methylphenidate on Attentional States in Children with ADHD," *J. of Child and Adolescent Psychopharmacology.* 14: 219-232, 2004.

Teicher et al., "Rate Dependency Revisited: Understanding the Effects of Methylphenidate in Children with Attention Deficit Hyperactivity Disorder," *J. of Child and Adolescent Psychopharmacology.* 13: 41-51, 2003.

International Search Report for PCT/US 07/08135. Mailed on Feb. 27, 2008.

Castellanos et al., "Varieties of Attention-Deficit/Hyperactivity Disorder-Related Intra-Individual Variability," *Biol. Psychiatry* 57:1416-1423, 2005.

Elia et al., "Methylphenidate and Dextroamphetamine Treatments of Hyperactivity: Are There True Nonresponders?" *Psychiatry Res.* 36:141-155, 1991.

Greenberg, L.M., "An Objective Measure of Methylphenidate Response: Clinical Use of the MCA," *Psychopharmacol. Bull.* 23:279-282, 1987.

Nuechterlein K.H., "Signal Detection in Vigilance Tasks and Behavioral Attributes Among Offspring of Schizophrenic Mothers and Among Hyperactive Children," *J. Abnorm. Psychol.* 92:4-28, 1983.

Rosvold et al., "A Continuous Performance Test of Brain Damage," *J. Consult. Clin. Psychol.* 20:343-350, 1956.

Teicher et al., "Objective Measurement of Hyperactivity and Attentional Problems in ADHD," *J. Am. Acad. Child Adolesc. Psychiatry* 35:334-342, 1996.

Teicher et al., "Novel Strategy for the Analysis of CPT Data Provides New Insight into the Effects of Methylphenidate on Attentional States in Children with ADHD," *J. Child Adolesc. Psychopharmacol.* 14:219-232, 2004.

International Preliminary Report on Patentability for PCT/US2007/008135, issued Oct. 8, 2008.

Written Opinion of the International Searching Authority for PCT/US2007/008135, completed Jan. 1, 2008, mailed Feb. 27, 2008.

Supplementary Partial European Search Report for EP 07754632, completed Feb. 15, 2010.

METHOD FOR DIAGNOSING ADHD AND RELATED BEHAVIORAL DISORDERS

CROSS-REFERENCE TO RELATED APPLICATIONS

The application claims benefit of U.S. Provisional Application No. 60/788,946 filed Apr. 4, 2006, which is incorporated herein by reference.

STATEMENT AS TO FEDERALLY SPONSORED RESEARCH

This invention was made with government support under Grant No. DA016934, awarded by the National Institutes of Health. The government has certain rights in the invention.

BACKGROUND OF THE INVENTION

The invention relates to methods and systems for the diagnosis of ADHD and related disorders.

Alterations in locomotor-activity levels and disturbances in rest-activity rhythms have long been recognized as an integral sign of many psychiatric disorders. For example, the hyperactivity of children with Attention-Deficit/Hyperactivity Disorder (ADHD) is most readily discernible as a failure to inhibit motor activity to low-levels.

Using precisely quantified movements, ADHD children have been shown to be 3-4 fold more active than controls. Teicher et al., *J. Am. Acad. Child Adolsec. Psychiatry* 35:334 (1996). However, the precise nature of their hyperactivity is unknown.

There is a need for reliable, inexpensive, and easy to use methods for diagnosing ADHD and related disorders.

SUMMARY OF THE INVENTION

The invention features methods and systems for the diagnosis of ADHD and related disorders. The methods and systems of the invention can also be used to ascertain how much benefit an individual would derive from a particular therapy.

In a first aspect, the invention features a method of diagnosing a disorder selected from ADHD and related disorders. The method includes the steps of: (i) using a motion analysis device to record movements of the subject; (ii) calculating the power spectral density of the oscillations in the movements; and (iii) on the basis of the spectral density, determining whether the subject has the disorder. Desirably, the spectral density is calculated over a frequency range between 0.01 and 0.5 Hz, 0.01 and 0.3 Hz, 0.01 and 0.1 Hz, or 0.05 and 0.2 Hz.

The invention features a method of diagnosing a disorder selected from ADHD and related disorders. The method includes the steps of: (i) using a motion analysis device to record movements of the subject; (ii) calculating the number of spikes in the movements; and (iii) on the basis of the number, determining whether the subject has the disorder.

The invention also features a method of diagnosing a disorder selected from ADHD and related disorders in a subject. The method includes the steps of: (i) using a motion analysis device to record movements of the subject; (ii) calculating the time intervals between spikes in the movements; and (iii) on the basis of the time intervals, determining whether the subject has the disorder.

In a related aspect, the invention features a method for assessing the efficacy of a medicament for the treatment of a disorder selected from ADHD and related disorders in a subject diagnosed with the disorder by (a) administering the medicament to the subject; (b) using a motion analysis device to record movements of the subject while medicated; (c) calculating the power spectral density of the oscillations in the movements; and (d) on the basis of the spectral density, determining whether the symptoms of the disorder are ameliorated by the medicament. The method can further include the steps of (e) prior to step (a), using a motion analysis device to record movements of the subject while unmedicated; (f) calculating the power spectral density of the oscillations in the movements; and (g) on the basis of the spectral density for step (c) and the spectral density for step (f), determining whether the symptoms of the disorder are ameliorated by the medicament.

In another aspect, the invention features a method for assessing the efficacy of a medicament for the treatment of a disorder selected from ADHD and related disorders in a subject diagnosed with the disorder by (a) administering the medicament to the subject; (b) using a motion analysis device to record movements of the subject while medicated; (c) calculating the number of spikes in the movements; and (d) on the basis of the number, determining whether the symptoms of the disorder are ameliorated by the medicament. The method can further include the steps of (e) prior to step (a), using a motion analysis device to record movements of the subject while unmedicated; (f) calculating the number of spikes in the movements; and (g) on the basis of the number for step (c) and the number for step (f), determining whether the symptoms of the disorder are ameliorated by the medicament.

The invention further features a method for assessing the efficacy of a medicament for the treatment of a disorder selected from ADHD and related disorders in a subject diagnosed with the disorder by (a) administering the medicament to the subject; (b) using a motion analysis device to record movements of the subject while medicated; (c) calculating the time intervals between spikes in the movements; and (d) on the basis of the time intervals, determining whether the symptoms of the disorder are ameliorated by the medicament. The method can further include the steps of (e) prior to step (a), using a motion analysis device to record movements of the subject while unmedicated; (f) calculating the time intervals between spikes in the movements; and (g) on the basis of the time intervals for step (c) and the time intervals for step (f), determining whether the symptoms of the disorder are ameliorated by the medicament.

In an embodiment of any of the above methods of the invention, the method further includes continuous performance testing of the subject while recording the movements.

In another embodiment of any of the above methods of the invention, the method includes measuring the activity of the subject using an infrared motion analysis system by tracking the movements of the subject's head, leg, elbow, shoulder, hand, or foot using a camera.

In any of the above methods, desirably, the number of spikes or the interval between spikes is calculated for two or more different amplitudes.

The invention also features a system for diagnosing a disorder selected from ADHD and related disorders in a subject. The system includes: (i) a motion analysis device; (ii) a device for receiving and storing motion data; and (iii) a processor provided with a computer program for analyzing the motion data to calculate the power spectral density of the oscillations.

The invention further features a system for diagnosing a disorder selected from ADHD and related disorders in a subject. The system includes: (i) a motion analysis device; (ii) a device for receiving and storing motion data; and (iii) a processor provided with a computer program for analyzing the motion data to calculate the number of spikes in the motion.

The invention features a system for diagnosing a disorder selected from ADHD and related disorders in a subject. The system includes: (i) a motion analysis device; (ii) a device for receiving and storing motion data; and (iii) a processor provided with a computer program for analyzing the motion data to calculate the time intervals between spikes in the motion.

In an embodiment of any of the systems of the invention, the motion analysis device includes a camera for measuring the activity of a subject using infrared light.

In any of the above aspects, a spike threshold can be set at an amplitude of greater than 1 mm/sec, 2 mm/sec, 3 mm/sec, 4 mm/sec, 5 mm/sec, 6 mm/sec, 7 mm/sec, or even 8 mm/sec.

In any of the above aspects, the disorder is ADD, ADHD, or Hyperkinetic Disorder.

As used herein, "ADHD or a related disorder" refers to disorders characterized by developmentally inappropriate degrees of inattention, overactivity, and impulsivity, such as Attention Deficit Hyperactivity Disorder—combined subtype, Attention Deficit Hyperactivity Disorder—predominantly hyperactive-impulsive subtype, Attention Deficit Hyperactivity Disorder—predominantly inattentive subtype, Attention Deficit Disorder with or without hyperactivity, Hyperkinetic Disorder, oppositional defiant disorder and conduct disorder. Attention Deficit Hyperactivity Disorder is a disorder characterized by inattention, impulsiveness, and hyperactivity. This disorder can impair social function, learning and/or development and is therefore now recognized as a serious problem. It is further recognized that many children with ADHD go on to develop other comorbid conditions or social problems in adulthood. In clinical terms ADHD is diagnosed if any one of the three main clinical features, inattention, over-activity, and impulsiveness, persists in two or more situations, e.g. in both a home and school environment (American Psychiatric Association. Diagnostic and Statistical Manual of Mental Disorders, Fourth Edition (DSM-IV) Washington D.C.; American Psychiatric Association, 1994). A diagnosis of Hyperkinetic Disorder is made only if all three of the main clinical features (inattention, over-activity and impulsiveness) have been present from an early age, persist in more than one situation (e.g. home and school) and impair function (The ICD-10 Classification of Mental and Behavioural Disorders: Diagnostic Criteria for Research. Geneva: World Health Organisation, 1993: 155-7).

As used herein, the term "spike" refers to a burst in the rate of movement in a subject that exceeds a threshold amplitude (e.g., 1 mm/sec). Spikes can be measured across the test period using any suitable time scale from milliseconds to minutes, preferably seconds, and amplitudes set to scale from a maximum value in the reference range to a suitable minimum of about 2× the baseline. Desirably, the spike amplitude is in the range of 1 mm/sec to 8 mm/sec (see FIG. 3 for exemplary time series data). The 'spike' continues until the movement falls back below the threshold amplitude level, ending the spike. Optionally, the spike doesn't end unless the movement remains below the threshold amplitude level for a set minimum amount of time (e.g., 240 msec to 1 sec). Such analysis can be accomplished using a variety of techniques, such as wavelet analysis, or by requiring the spike train to remain below threshold for a minimum time period.

Other features and advantages of the invention will be apparent from the following detailed description, the drawings, and the claims.

DETAILED DESCRIPTION

A characteristic signature of ADHD and related disorders has been found in the movements of subjects suffering from such disorders. The invention exploits the relationship between the spectral density of multisecond oscillations, number of spikes, and/or the intervals between spikes and ADHD to provide methods and system for the diagnosis of ADHD and related disorders. The methods and systems of the invention can also be used to ascertain how much benefit an individual would derive from a particular therapeutic regimen (see Example 1).

Systems

Figure 1:
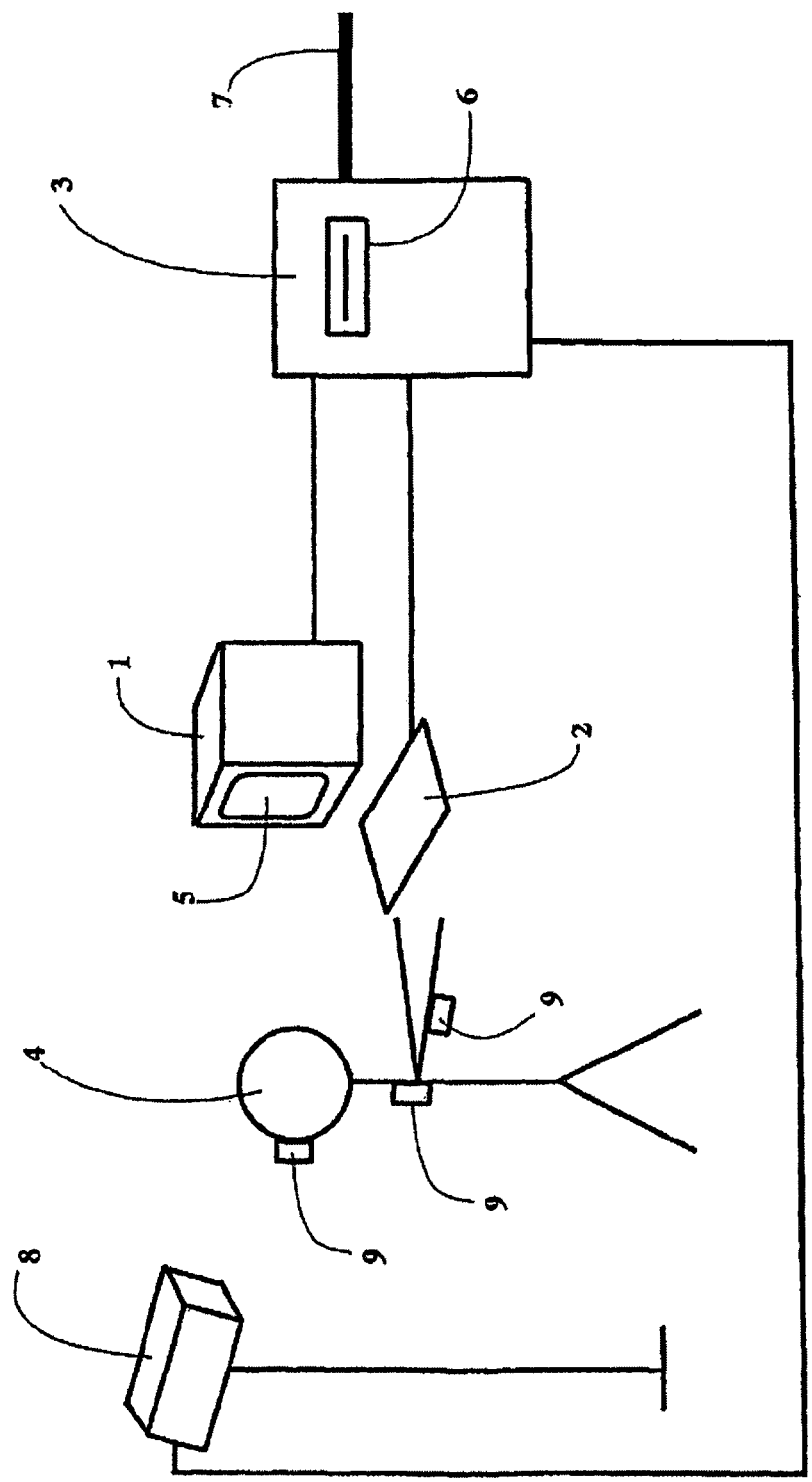
FIG. 1 depicts a system for performing a method of the invention. The system includes a motion analysis device 8 that is connected to the computer 3 and positioned so as to record the movements of the subject 4.

An embodiment of a system for performing a method of the invention is shown in FIG. 1. The system includes a motion analysis device 8 that is connected to the computer 3 and positioned so as to record the movements of the subject 4. Any video camera or other motion-sensing device capable of detecting the movements of the subject 4 can be used. For instance, the motion analysis device 8 can be an infrared motion analysis system that includes a high-resolution CCD infrared video camera, an infrared strobe, and a video processor that provides hardware analysis of the video signal and outputs data to the computer 3. Such infrared motion analysis systems are known in the art, and are specifically designed to detect and record the precise vertical and horizontal position of small, light-weight infrared reflective markers 9. These markers 9 are attached to the subject 4 at various points, such as the head, shoulders, and elbows. As the subject 4 moves these portions of his or her body, the IR motion analysis system detects changes in the positions of the markers 9 and relays this information to the computer 3. Successive marker coordinates can be stored in the computer 3 and analyzed.

The computer 3 can be a stand-alone personal computer, preferably with high computational capacity microprocessors. Alternatively, a minicomputer or mainframe computer can be used. The computer 3 can have a disc drive 6 into which the software that analyzes the subject's input's and/or movement patterns is loaded. In a preferred embodiment, the computer 3 has a connection 7 to a network of computers, such as a global computer network. This allows the computer 3 to exchange data with other computers connected to the network. In other preferred embodiments, the computer network is a local area network, a wide area network, an intranet, or an extranet. Thus, a subject may be tested not only in a clinical setting, but also at a remote location, such as the home, school, or workplace, thereby eliminating the inconvenience of traveling long distances for testing.

The system may also include a monitor 1 that is a capable of displaying visual images on a screen 5. The monitor 1 is attached to a computer 3 and is positioned in proximity to a subject 4, so that the subject 4 may view the images displayed on the monitor screen 5. The computer 3 can be programmed to display a desired sequence of images, to which the subject 4 is instructed to respond by activating an input device 2 that is also attached to the computer 3 and is controllable by the subject 4. The input device 2 can be, for example, a standard computer keyboard, a hand-held plunger switch, or a large, easy-to-hit switch several (2-3) inches in length. When activated, the input device 2 sends the subject's inputs to the computer 3 which stores and analyzes the incidents of device activation.

Motion Detection System

A motion detection system is used to track the movement of the head an/or lower extremities of the individual being tested. Any video camera or other motion-sensing device capable of detecting the movements of the test subject can be used. For example, the motion analysis device can be an infrared motion analysis system (e.g., Qualisys, Glastonbury, Conn.) that includes a high-resolution CCD infrared video camera, an infrared strobe, and a video processor that provides hardware analysis of the video signal and outputs data to a computer. Such infrared motion analysis systems are known in the art, and are specifically designed to detect and record the precise vertical and horizontal position of small, light-weight infrared reflective markers. These markers are attached to the subject at various points, such as the head, shoulders, arms, legs, and feet. As the subject moves these portions of his or her body, the IR motion analysis system detects changes in the positions of the markers and relays this information to a computer. Successive marker coordinates can be stored in the computer and analyzed. Desirably, the camera is positioned in front of the subject, who is preferably in a seated position. The camera is also desirably positioned in such a manner that it can capture movements of the reflective markers in three dimensions, including movements towards and away from the display device. The motion analysis device can also include a second camera that can be used in combination with the first camera to better differentiate three dimensional movement. Adults with ADHD or related disorders can manifest hyperactivity solely through excess movement of their lower extremities while seated. Therefore, the first camera can be used to track the movement of the subject's legs and/or feet or a second camera can be used to track the movement of the subject's lower extremities while the first camera tracks upper body movements. Alternatively, visible light and standard video camera are used to measure the movement of a subject, or an accelerometer is used.

Movement patterns can be analyzed using procedures described by Teicher et al., *J. Am. Acad. Child Adolsec. Psychiatry* 35:334 (1996), which are based on the concept of microevents. A new microevent begins whenever the marker moves more than a predetermined distance from the location of the previous microevent, and is defined by its position and duration.

Figure 3:
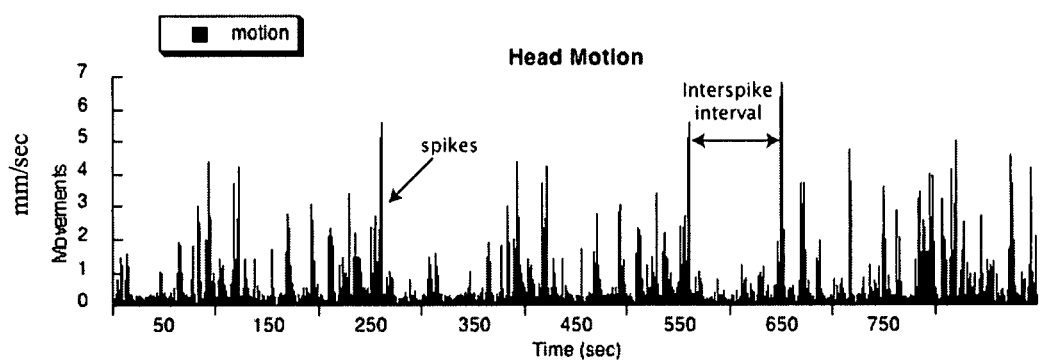
FIG. 3 is a graph showing the rate (mm/sec) of head motor activity of a subject as a function of time. The activity data exhibits brief intermittent high-amplitude spikes.

Exemplary data showing the head motion of a subject is provided in FIG. 3. First, a threshold amplitude level is set (e.g., 1 mm/sec) and the number of spikes in the movements and/or the interval between spikes in the movements is calculated.

Individuals with ADHD have an increased number of spikes at any select threshold, and have a shorter average interspike interval (see Example 1) in comparison to individuals without ADHD.

Furthermore, the efficacy of a therapeutic regimen can be assessed using the methods and systems of the invention. An effective treatment is one which reduces the number of spikes, and lengthens the average interspike interval across the different threshold values.

Optionally, the methods of the invention are used to create a curve of 'spike' numbers versus threshold amplitude, which is then compared to a normative database to ascertain whether the individual's profile deviates significantly from normal subjects. The comparison can be made using neural network techniques, or by using a variety of statistical techniques, such as logistic regression analysis, cluster analysis, discriminant analysis, or optimal data analysis, to see if the individuals profile better resembles normal or ADHD.

A variety of statistical techniques can be used in connection with the methods and systems of the invention. For example, the movement time series can be analyzed using a mathematical techniques such as Fourier Transform, Wigner-Wille Transform, or wavelet analysis to decompose time series from time domain into frequency domain. Once converted to the frequency domain, the amount of spectral power can be calculated for the oscillations in the movements. Desirably, the spectral power is calculated within a low-frequency (multisecond oscillation) domain (e.g., between 0.01 and 0.5 Hz).

Individuals with ADHD exhibit an increase in the spectral power of the low frequency motion of the subject in comparison to individuals without ADHD. Spectral power can also be used to assess the efficacy of a therapeutic regimen. An effective treatment is one which reduces the low frequency motion of the subject.

Continuous Performance Test

The subject is, desirably, engaged in a continuous performance test (CPT) while the motor activity of the subject is monitored. For example, subject's visual attention can be tested by displaying a series of visual stimuli, to which the subject is instructed to respond. Typically, the stimuli are of two types, and the subject is instructed to respond to only one of them. Data are collected for each stimulus presented including the type of stimulus, whether or not the subject responded, and if so, how long the subject took to respond. The continuous performance attention test has been in use since the mid 50's (Rosvold et al., *J. Consulting and Clinical Psychology* 20:343 (1956)), with computerized versions available in the 1970's (Greenberg, *Psychopharmacol. Bull.* 23:279 (1987)).

The CPT results can include measuring errors of commission, errors of omission, and mean correct reaction time with standard deviation. More sophisticated CPT measures, derived from signal detection theory can include a calculation of stimulus sensitivity (d') (see, for example, Nuechterlein, *J. Abnorm. Psychol.* 92:4 (1983)).

Analysis of the CPT results can also include assessing the pattern or fluctuation in attentional states by a subject during a test period. This approach is described in U.S. Pat. No. 6,685,652, incorporated herein by reference.

The methods of the invention may be used alone, together, or in conjunction with other well-known psychological tests for determining attention or reaction time. Testing of the subject's performance may be conducted with or without providing corrective feedback to the subject during performance of the CPT.

Therapy and Dosing Regimens

The methods and systems of the invention can provide information on the efficacy of any particular therapy in an individual. For example, using the methods of the invention it can be possible to determine how a subject would respond to any of the different long acting stimulant preparations (e.g., Concerta™ 18, 36, and 54 mg; Metadate CD™ 20, 40, 60 mg; Ritalin-LA™ 10-60 mg) or combinations, such as Ritalin-LA™ 40 mg taken at 8 am and Ritalin™ immediate release 15 mg taken at 4 PM. These assessments are made based upon the degree of improvement in a subject's motor activity and, optionally, performance on CPT testing.

If a test subject fails to show substantial benefits on one class of stimulants (i.e., methylphenidate versus amphetamine derivatives, such as dextroamphetamine or Adderall), the subject can be tested on a separate day on a drug from the other class of stimulants. Clinical research has shown that patients with ADHD often respond better to one class of stimulants than another, and that a significant number of patients with ADHD will have a very beneficial response to one class of agents but will fail to respond to the other class, or will have side-effects on only one class (see, for example, Elia et al., *Psychiatry Res.* 36:141 (1991)).

The following example is put forth so as to provide those of ordinary skill in the art with a complete disclosure and description of how the methods and compounds claimed herein are performed, made, and evaluated, and are intended to be purely exemplary of the invention and are not intended to limit the scope of what the inventors regard as their invention.

Example 1

Motor Activity in ADHD Children with and without Methylphenidate Therapy

Sixty-two boys (10.6±1.1 years of age, range 9-12) meeting DSM-IV criteria for ADHD, participated in this IRB-approved study. Head movements were recorded prior to, and following, a probe dose of 0.4 mg/kg methylphenidate, while subjects were seated and performing a Go/No-Go CPT (Teicher et al., *J. Child Adolesc. Psychopharmacol.* 14(2):219-32 (2004)). An infrared motion analysis system tracked and recorded vertical and horizontal position of a head marker 50 times per second to a resolution of 1 mm.

Figure 2A:
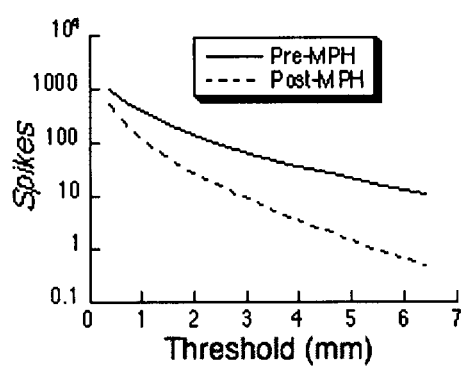
FIG. 2a is a graph showing that methylphenidate therapy reduces the number of spikes exhibited in the motor activity of children with ADHD. See Example 1.
Figure 2B:
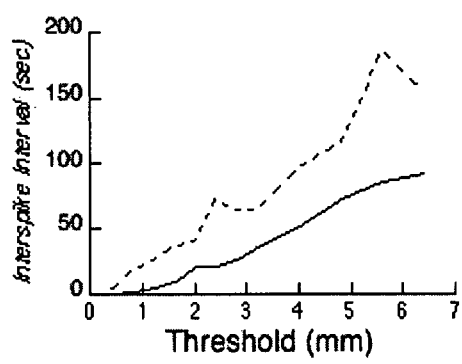
FIG. 2b is a graph showing that methylphenidate therapy increases the interspike interval exhibited in the motor activity of children with ADHD. See Example 1.

ADHD children had episodic bursts of movement, which occurred as discrete spikes. Across spike amplitude threshold children with ADHD had from 2× (low threshold)–44× (high threshold) more spikes off medication (MPH effect: $F_{1,61}=73.87$, $p<10^{-11}$, see FIG. 2a). Spikes had a typical amplitude of between 1.6-6.4 mm, mean duration of 240 msec, and an interspike interval (ISI) of 10-100 seconds (x=26.0 sec). MPH therapy increased the interspike interval by 2-4× (e.g., 2 mm threshold, ISI 14.5±23.5 vs. 43.0±56.8 sec, F1,39=8.82, p<0.005, see FIG. 2b).

Prior to treatment about 25% of the activity of ADHD children occurred as discrete spikes. MPH reduced this by 80% by markedly attenuating number of spikes and increasing interspike intervals.

Other Embodiments

All publications, patents, and patent applications mentioned in this specification are herein incorporated by reference to the same extent as if each independent publication or patent application was specifically and individually indicated to be incorporated by reference.

While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and may be applied to the essential features hereinbefore set forth, and follows in the scope of the claims.

Other embodiments are within the claims.

What is claimed is:

1. A method of diagnosing ADHD or a related disorder in a subject comprising the steps of:
    (i) using a motion analysis device to record movements and produce motion data of said subject and transmitting said motion data to a computer for analysis;
    (ii) receiving the results of said analysis, wherein said analysis comprises calculating from said motion data the power spectral density of the oscillations in said movements; and
    (iii) on the basis of said spectral density, diagnosing whether said subject has ADHD or a related disorder, wherein said spectral density is calculated over a frequency range between 0.01 and 0.5 Hz.

2. The method of claim 1, wherein said spectral density is calculated over a frequency range between 0.01 and 0.3 Hz.

3. The method of claim 2, wherein said spectral density is calculated over a frequency range between 0.01 and 0.1 Hz.

4. The method of claim 2, wherein said spectral density is calculated over a frequency range between 0.05 and 0.2 Hz.

5. A method of diagnosing ADHD or a related disorder in a subject comprising the steps of:
    (i) using a motion analysis device to record movements and produce motion data of said subject and transmitting said motion data to a computer for analysis;
    (ii) receiving the results of said analysis, wherein said analysis comprises calculating from said motion data the number of spikes in said movements; and
    (iii) on the basis of said number, diagnosing said whether subject has ADHD or a related disorder wherein said spikes are bursts in the rate of said movements by said subject exceeding a threshold amplitude of greater than 1 mm/second.

6. A method of diagnosing ADHD or a related disorder in a subject comprising the steps of:
    (i) using a motion analysis device to record movements and produce motion data of said subject and transmitting said motion data to a computer for analysis;
    (ii) receiving the results of said analysis, wherein said analysis comprises calculating from said motion data the time intervals between spikes in said movements; and
    (iii) on the basis of said time intervals, diagnosing whether said subject has ADHD or a related disorder wherein said spikes are bursts in the rate of said movements by said subject exceeding a threshold amplitude of greater than 1 mm/second.

7. The method of claim 5 or 6, wherein said spikes have an amplitude of greater than 3 mm/second.

8. The method of claim 5, wherein said number of spikes is calculated for two or more different amplitudes.

9. The method of claim 1, 5, or 6, wherein said disorder is ADD, ADHD, or Hyperkinetic Disorder.

10. The method of claim 1, 5, or 6, further comprising continuous performance testing of said subject while recording said movements.

11. The method of claim 1, 5, or 6, wherein step (i) comprises measuring the activity of said subject using an infrared motion analysis system by tracking the movements of said subject's head, leg, elbow, shoulder, hand, or foot using a camera.

12. A method for assessing the efficacy of a medicament for the treatment of ADHD or a related disorder in a subject diagnosed with said disorder, said method comprising:
    (a) administering said medicament to said subject;
    (b) using a motion analysis device to record movements and produce motion data of said subject while medicated and transmitting said motion data to a computer for analysis;

(c) receiving the results of said analysis, wherein said analysis comprises calculating from said motion data the power spectral density of the oscillations in said movements; and (d) on the basis of said spectral density, determining the effect of said medicament on said subject diagnosed with said disorder, wherein said spectral density is calculated over a frequency range between 0.01 and 0.5 Hz.

13. The method of claim 12, further comprising:

(e) prior to step (a), using a motion analysis device to record movements and produce motion data of said subject while unmedicated and transmitting said motion data to a computer for analysis;

(f) receiving the results of said analysis, wherein said analysis comprises calculating from said motion data the power spectral density of the oscillations in said movements; and (g) on the basis of said spectral density for step (c) and said spectral density for step (f), determining the effect of said medicament on said subject.

14. A method for assessing the efficacy of a medicament for the treatment of ADHD or a related disorder in a subject diagnosed with said disorder, said method comprising:

(a) administering said medicament to said subject;

(b) using a motion analysis device to record movements and produce motion data of said subject while medicated and transmitting said motion data to a computer for analysis;

(c) receiving the results of said analysis, wherein said analysis comprises calculating from said motion data the number of spikes in said movements; and (d) on the basis of said number, determining the effect of said medicament on said subject diagnosed with said disorder wherein said spikes are bursts in the rate of said movements by said subject exceeding a threshold amplitude of greater than 1 mm/second.

15. The method of claim 14, further comprising:

(e) prior to step (a), using a motion analysis device to record movements and produce motion data of said subject while unmedicated and transmitting said motion data to a computer for analysis;

(f) receiving the results of said analysis, wherein said analysis comprises calculating from said motion data said number of spikes in said movements; and (g) on the basis of said number for step (c) and said number for step (f), determining the effect of said medicament on said subject.

16. A method for assessing the efficacy of a medicament for the treatment of ADHD or a related disorder in a subject diagnosed with said disorder, said method comprising:

(a) administering said medicament to said subject;

(b) using a motion analysis device to record movements and produce motion data of said subject while medicated and transmitting said motion data to a computer for analysis;

(c) receiving the results of said analysis, wherein said analysis comprises calculating from said motion data the time intervals between spikes in said movements; and (d) on the basis of said time intervals, determining the effect of said medicament on said subject diagnosed with said disorder wherein said spikes are bursts in the rate of said movements by said subject exceeding a threshold amplitude of greater than 1 mm/second.

17. The method of claim 16, further comprising:

(e) prior to step (a), using a motion analysis device to record movements and produce motion data of said subject while unmedicated and transmitting said motion data to a computer for analysis;

(f) receiving the results of said analysis, wherein said analysis comprises calculating from said motion data the time intervals between said spikes in said movements; and (g) on the basis of said time intervals for step (c) and said time intervals for step (f), determining the effect of said medicament on said subject.

18. A system for diagnosing a disorder selected from ADHD or a and related disorders in a subject comprising:

(i) a motion analysis device;

(ii) a device for receiving and storing motion data; and (iii) a processor provided with a computer program for analyzing said motion data to calculate the power spectral density of the oscillations in said motion over a frequency range between 0.01 and 0.5 Hz; and (iv) an output providing a diagnosis of ADHD or a related disorder.

19. A system for diagnosing ADHD or a related disorder in a subject comprising:

(i) a motion analysis device;

(ii) a device for receiving and storing motion data;

(iii) a processor provided with a computer program for analyzing said motion data to calculate the number of spikes in said motion; and (iv) an output providing a diagnosis of ADHD or a related disorder, wherein said spikes are bursts in the rate of said movements by said subject exceeding a threshold amplitude of greater than 1 mm/second.

20. A system for diagnosing ADHD or a related disorder in a subject comprising:

(i) a motion analysis device;

(ii) a device for receiving and storing motion data; and (iii) a processor provided with a computer program for analyzing said motion data to calculate the time intervals between spikes in said motion; and (iv) an output providing a diagnosis of ADHD or a related disorder, wherein said spikes are bursts in the rate of said movements by said subject exceeding a threshold amplitude of greater than 1 mm/second.

21. The system of any of claims 18-20, wherein said motion analysis device comprises a camera for measuring the activity of a subject using infrared light.

* * * * *